(12) United States Patent
Elsbach et al.

(10) Patent No.: US 6,287,811 B1
(45) Date of Patent: *Sep. 11, 2001

(54) BIOLOGICALLY ACTIVE BACTERICIDAL/PERMEABILITY-INCREASING PROTEIN FRAGMENTS

(75) Inventors: Peter Elsbach; Jerrold Weiss, both of New York, NY (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/309,217

(22) Filed: May 10, 1999

Related U.S. Application Data

(63) Continuation of application No. 08/361,299, filed on Jan. 23, 1995, now Pat. No. 5,948,408, which is a continuation of application No. 08/007,837, filed on Jan. 22, 1993, now Pat. No. 5,641,784, which is a continuation of application No. 07/805,031, filed on Dec. 11, 1991, now Pat. No. 5,198,541, which is a division of application No. 07/762,730, filed on Sep. 17, 1991, now abandoned, which is a continuation of application No. 07/228,035, filed on Aug. 5, 1998, now abandoned, which is a continuation-in-part of application No. 07/084,335, filed on Aug. 11, 1987, now abandoned.

(51) Int. Cl.[7] .................................................... C12P 21/06

(52) U.S. Cl. ................... 435/69.1; 435/69.3; 435/320.1; 435/243; 435/252.1; 435/325; 536/23.5; 536/23.1; 530/350

(58) Field of Search ................................ 435/69.1, 69.3, 435/320.1, 243, 252.1, 325; 536/23.5, 23.1; 530/350

(56) References Cited

U.S. PATENT DOCUMENTS

| | | |
|---|---|---|
| 5,087,569 | 2/1992 | Gabay et al. . |
| 5,089,274 | 2/1992 | Marra et al. . |
| 5,126,257 | 6/1992 | Gabay et al. . |
| 5,171,739 | 12/1992 | Scott et al. ............................. 514/12 |
| 5,198,541 * | 3/1993 | Elsbach et al. . |
| 5,308,834 | 5/1994 | Scott et al. ............................. 514/12 |
| 5,334,584 | 8/1994 | Scott et al. . |
| 5,641,874 * | 6/1997 | Elsbach et al. . |

FOREIGN PATENT DOCUMENTS 0272489   6/1988   (EP) .

OTHER PUBLICATIONS

Elsbach et al., "Separation and Purification of a Potent Bactericidal/Permeability–Increasing Protein and a Closely Associated Phospholipase A2 from Rabbit Polymorphonuclear Leukocytes", *J. Biol. Chem.*, 254(21): 11000–11009 (1979).

Elsbach et al., "Bactericidal /Permebility Increasng Protein (BPI) of Granulocytes: Structure and Function," *Bacteria–Host Cell Interaction*, M.A. Horwitz, (ed.), UCLA Symp. Mol. Biol., New Ser., vol. 64 Park City, VT (Feb. 13–19, 1987), Alan R. Liss, N.Y., pp. 47–60 (1988).

Elsbach et al., "Phaocytic Cells: Oxygen– Independent Antimicrobial Systems", Chapter 24, in *Inflammation: Basic Principles and Clinical Correlates*, Gallin et al., (Eds.), Raven Press, Ltd., New York, pp. 445–470 (1988).

Gabay et al., "Antimicrobial Proteins From the Membrane of the Azurophil Granule of Human Neutrophils," 22nd Meet. Eur. Soc. Clin. Inves., Graz, Austria (Apr. 20–23, 1988), *European Journal of Clinical Investigation*, 18(2):A38 (1988) (ABSTRACT 187).

Gray et al., "Cloning of the Gene of the Human Bactericidal/Permeability Increasing Protein and Identification of Structure–Function Relationships," 101st Ann. Natl. Meet. Assoc. Am. Physicians (Apr. 29–May 2, 1988) *Clinical Research*. 36(3):620A (Apr., 1988) (ABSTRACT).

Ooi et al., "A 25–kDa $NH_2$–terminal Fragment Carries All the Antibacterial Activities of the Human Neutrophil 60–kDa Bactericidal/Permeability–Increasing Protein," *J. Biol. Chem.*, 262(31):14891–14894 (1987).

Shafer et al., "Lipid A and Resistance of *Salmonella typhimurium* to Antimicrobial Granule Proteins of Human Neutrophil Granulocytes," *Infection and Immunity*, 43:834–838 (Mar., 1984).

Spitznagel et al., "A Monoclonal Antibody That Inhibits the Antimicrobial Action of a 57 KD Cationic Protein of Human Polymorphonuclear Leukocytes," *Journal of Immunology*, 139(4): 1291–1296 (Aug. 15, 1987).

Suggs et al., "Use of synthetic oligonucleotides as hybridization probes: Isolation of cloned cDNA sequences for human $\beta_2$–microglobulin," *Proc. Nat'l Acad. Sci.*, USA, 78:6613–6617 (Nov., 1981).

Tobias et al., "Isolation of a Lipopolyxaccharide–Binding Acute Phase Reactant From Rabbit Serum," *Journal of Experimental Medicine*, 164:777–793 (Sep. 1986).

Tobias et al., "A Family of Lipopolysaccharide Binding Proteins Involved in Responses to Gram–negative Sepsis," *Journal of Biological Chemistry*, 263(27): 13479–13481 (1988).

Ulevitch et al., "Interactions of Bactericidal Lipoplysaccharides With Serum Proteins," *Bacterial Endotoxins: Pathophysiological Effects, Clinical Significance, and Pharmacological Control*, 272:309–318 (1988).

Ulevitch et al., "A Family of LPS Binding Proteins Involved in Responses to Gram Negative Sepsis and Endotoxemia," *FASEB Journal*, 2:A991 (1988), 72nd Ann. Meet. Fed. Am. Soc. Exp. Bio., Las Vegas, NV (May 1–5, 1988) (ABSTRACT 4039).

(List continued on next page.)

Primary Examiner—Jennifer Graser
(74) Attorney, Agent, or Firm—Marshall, O'Toole Gerstein, Murray & Borun

(57) ABSTRACT

A purified, isolated DNA sequence encoding human bactericidal/permeability-increasing protein and biologically-active fragments thereof is provided.

3 Claims, 10 Drawing Sheets

OTHER PUBLICATIONS

Veld et al., "Effects of the Bactericidal/Permability–Increasing Protein of Polymorphonuclear Leukocytes on Isolated Bacterial Cytoplasmic Membrane Vesicles" *Infection and Immunity*, 56(5) :1203–1208 (1988).

Weiss et al., "Partial Characterization and Purification of a Rabbit Granulocyte Factor that Increases Permeability of *Escherichia coli,*" *Journal of Clinical Investigation,* 55:33–42 (Jan., 1975).

Weiss et al., "Purification and Characterization of a Potent Bactericidal and Membrane Active Protein from the Granules of Human Polymorphonuclear Leukocytes," *Journal of Biological Chemistry,* 253(8):2664–2672 (Apr. 25, 1978).

Weiss et al., "Resistance of Gram–Negative Bacteria to Purified Bacteridal Leukocyte Proteins," *J. Clin. Invest.,* 65:pp. 619–628 (1980).

Weiss et al., "Sensitivity of K1–Encapsulated *Escherichia coli* to Killing by the Bactericidal/Permeability–Increasing Protein Of Rabbit And Human Neutrophils", *Infection and Immunity,* 38(3) pp. 1149–1153 (1982).

Weiss et al., "Role of Charge and Hydrophobic Interactions in the Action of the Bactericidal/Permeability–Increasing Protein of Neutrophils on Gram–Negative Bacteria", *J. Clin. Invest.* 71:pp. 540–549 (1983).

Weiss et al., "The Role of Lipoplysaccharides in the Action of the Bactericidal/Permeability–Increasing Neutrophil Protein on the Bacterial Envelope" *The Journal of Immunology* 132(6) pp. 3109–3115 (1984).

Weiss et al., "Structural & Immunological Dissection of Highly Conserved Bactericidal/Permeability–Increasing Proteins," *Clin. Research,* 34:537A (1986), 43$^{rd}$ Ann. Natl. Meet. Am. Fed. Clin. Res. (May 2–5, 1986).

Weiss et al., "Cellular & Subcellular Localization of the Neutrophil Bacterial/Permeability–Increasing Protein," *Clin. Research.* 34–537A (1986), 43$^{rd}$ Ann. Natl. Meet. Am. Fed. Clin. Res., (May 2–5, 1986).

Weiss et al., "Environmental Modulation of Lipopolysaccharide Chain Length Alters the Ssensitivy of *Escherichia coli* to the Neutorphil Bactericidal/Permeability–Increasing Protein," *Infection and Immunity,* 51(2) pp. 594–599 (1986).

* cited by examiner

Bosterial Viability

14C-Amino Acid Incorp. (-Actinomycin D)

14C-Amino Acid Incorp. (+Actinomycin D)

Phospholipid Hydrolysis

FIG. 5A

```
                                                          -30
                                                     met  arg  glu  asn
  1 CAGGCCTTGAGGTTTTGGCAGCTCTGGAGG                   ATG  AGA  GAG  AAC -10
      leu  met  val  leu  val  ala  ile  gly  thr  ala  val  thr
 82   CTG  ATG  GTG  CTC  GTC  GCC  ATA  GGC  ACC  GCC  GTG  ACA 20
      Lys  Gly  Leu  Asp  Tyr  Ala  Ser  Gln  Gln  Gly  Thr  Ala
157   AAG  GGC  CTG  GAC  TAC  GCC  AGC  CAG  CAG  GGG  ACG  GCC 40
      Tyr  Ser  Asp  Ser  Phe  Lys  Ile  Lys  His  Leu  Gly  Lys
232   TAC  TCA  GAC  AGC  TTT  AAG  ATC  AAG  CAT  CTT  GGG  AAG 70
      Gln  Leu  Pro  Ser  Ser  Gln  Ile  Ser  Met  Val  Pro  Asn
307   CAG  CTT  CCC  AGT  TCC  CAG  ATA  AGC  ATG  GTG  CCC  AAT 90
      Ile  Ser  Gly  Lys  Trp  Lys  Ala  Gln  Lys  Arg  Phe  Leu
382   ATC  AGC  GGG  AAA  TGG  AAG  GCA  CAA  AAG  AGA  TTC  TTA 120
      Ser  Ile  Ser  Ala  Asp  Leu  Lys  Leu  Gly  Ser  Asn  Pro
457   TCC  ATT  TCG  GCT  GAT  CTG  AAG  CTG  GGC  AGT  AAC  CCC 140
      Ser  His  Ile  Asn  Ser  Val  His  Val  His  Ile  Ser  Lys
532   AGC  CAC  ATC  AAC  AGT  GTC  CAC  GTG  CAC  ATC  TCA  AAG 170
      Ile  Glu  Ser  Ala  Leu  Arg  Asn  Lys  Met  Asn  Ser  Gln
607   ATT  GAG  TCT  GCG  CTT  CGA  AAC  AAG  ATG  AAC  AGC  CAG 190
      Gln  Pro  Tyr  Phe  Gln  Thr  Leu  Pro  Val  Met  Thr  Lys
682   CAA  CCT  TAT  TTC  CAG  ACT  CTG  CCA  GTA  ATG  ACC  AAA 220
      Pro  Pro  Ala  Thr  Thr  Ala  Glu  Thr  Leu  Asp  Val  Gln
757   CCT  CCA  GCA  ACC  ACG  GCT  GAG  ACC  CTG  GAT  GTA  CAG 240
      Pro  Pro  Phe  Ala  Pro  Pro  Val  Met  Glu  Phe  Pro  Ala
832   CCT  CCC  TTT  GCT  CCA  CCA  GTG  ATG  GAG  TTT  CCC  GCT
```

FIG. 5B

```
                                              270
     Phe Phe Asn Thr Ala Gly Leu Val Tyr Gln Glu Ala
 907 TTC TTC AAC ACA GCC GGG CTT GTA TAC CAA GAG GCT

290
     Lys Glu Ser Lys Phe Arg Leu Thr Thr Lys Phe Phe
 982 AAG GAG TCC AAA TTT CGA CTG ACA ACC AAG TTC TTT

320
     Met Lys Ile Gln Ile His Val Ser Ala Ser Thr Pro
1057 ATG AAG ATA CAG ATC CAT GTC TCA GCC TCC ACC CCG

340
     Pro Ala Val Asp Val Gln Ala Phe Ala Val Leu Pro
1132 CCT GCC GTG GAT GTC CAG GCC TTT GCC GTC CTC CCC

370
     Thr Thr Gly Ser Met Glu Val Ser Ala Glu Ser Asn
1207 ACA ACT GGT TCC ATG GAG GTC AGC GCC GAG TCC AAC

390
     Glu Leu Lys His Ser Asn Ile Gly Pro Phe Pro Val
1282 GAA CTG AAG CAC TCA AAT ATT GGC CCC TTC CCG GTT

420
     Leu Val Leu Pro Arg Val Asn Glu Lys Leu Gln Lys
1357 CTT GTG CTG CCC AGG GTT AAC GAG AAA CTA CAG AAA

440
     Asn Val Val Leu Gln Pro His Gln Asn Phe Leu Leu
1432 AAC GTA GTG CTT CAG CCT CAC CAG AAC TTC CTG CTG

1511 GGGGGCTGTCAGCCGCACCTGTTCCTGATGGGCTGTGGGGCACCGGC

1611 TTCTTCGACTCAGATTCAGAAATGATCTAAACACGAGGAAACATTAT

1711 GCTAAGGCTGCAGAGATATTTCCTCCAGGAATCGTGTTTCAATTGTA

1811 GTG---poly-A tail
```

FIG. 5C

```
                                    -20
    met ala arg gly pro cys asn ala pro arg trp val ser
    ATG GCC AGG GGC CCT TGC AAC GCG CCG AGA TGG GTG TCC 1                                           10
    ala ala Val Asn Pro Gly Val Val Val Arg Ile Ser Gln
    GCG GCC GTC AAC CCT GGC GTC GTG GTC AGG ATC TCC CAG 30
    Ala Leu Gln Lys Glu Leu Lys Arg Ile Lys Ile Pro Asp
    GCT CTG CAG AAG GAG CTG AAG AGG ATC AAG ATT CCT GAC 50                                          60
    Gly His Tyr Ser Phe Tyr Ser Met Asp Ile Arg Glu Phe
    GGG CAT TAT AGC TTC TAC AGC ATG GAC ATC CGT GAA TTC 80
    Val Gly Leu Lys Phe Ser Ile Ser Asn Ala Asn Ile Lys
    GTG GGC CTT AAG TTC TCC ATC AGC AAC GCC AAT ATC AAG 100                                         110
    Lys Met Ser Gly Asn Phe Asp Leu Ser Ile Glu Gly Met
    AAA ATG AGC GGC AAT TTT GAC CTG AGC ATA GAA GGC ATG 130
    Thr Ser Gly Lys Pro Thr Ile Thr Cys Ser Ser Cys Ser
    ACG TCA GGC AAG CCC ACC ATC ACC TGC TCC AGC TGC AGC 150                                         160
    Ser Lys Val Gly Trp Leu Ile Gln Leu Phe His Lys Lys
    AGC AAA GTC GGG TGG CTG ATC CAA CTC TTC CAC AAA AAA 180
    Val Cys Glu Lys Val Thr Asn Ser Val Ser Ser Lys Leu
    GTC TGC GAG AAA GTG ACC AAT TCT GTA TCC TCC AAG CTG 200                                         210
    Ile Asp Ser Val Ala Gly Ile Asn Tyr Gly Leu Val Ala
    ATA GAT TCT GTG GCT GGA ATC AAC TAT GGT CTG GTG GCA 230
    Met Lys Gly Glu Phe Tyr Ser Glu Asn His His Asn Pro
    ATG AAG GGG GAG TTT TAC AGT GAG AAC CAC CAC AAT CCA 250                                         260
    Ala His Asp Arg Met Val Tyr Leu Gly Leu Ser Asp Tyr
    GCC CAT GAC CGC ATG GTA TAC CTG GGC CTC TCA GAC TAC
```

FIG. 5D

|     |     |     |     |     |  280 |     |     |     |     |     |     |
|-----|-----|-----|-----|-----|-----|-----|-----|-----|-----|-----|-----|
| Gly | Val | Leu | Lys | Met | Thr | Leu | Arg | Asp | Asp | Met | Ile | Pro |
| GGG | GTC | TTG | AAG | ATG | ACC | CTT | AGA | GAT | GAC | ATG | ATT | CCA |

300                                                    310
Gly Thr Phe Leu Pro Glu Val Ala Lys Lys Phe Pro Asn
GGA ACC TTC CTA CCT GAG GTG GCC AAG AAG TTT CCC AAC

330
Pro His Leu Ser Val Gln Pro Thr Gly Leu Thr Phe Tyr
CCA CAC CTG TCT GTG CAG CCC ACC GGC CTT ACC TTC TAC

360
Asn Ser Ser Leu Ala Ser Leu Phe Leu Ile Gly Met His
AAC TCC TCC CTG GCT TCC CTC TTC CTG ATT GGC ATG CAC

380
Arg Leu Val Gly Glu Leu Lys Leu Asp Arg Leu Leu Leu
AGG CTT GTT GGA GAG CTC AAG CTG GAT AGG CTG CTC CTG 400                                            410
Glu Leu Leu Gln Asp Ile Met Asn Tyr Ile Val Pro Ile
GAA TTG CTG CAG GAT ATC ATG AAC TAC ATT GTA CCC ATT

430
Gly Phe Pro Leu Pro Thr Pro Ala Arg Val Gln Leu Tyr
GGC TTC CCT CTC CCG ACG CCG GCC AGA GTC CAG CTC TAC

450
Phe Gly Ala Asp Val Val Tyr Lys
TTC GGT GCA GAC GTT GTC TAT AAA TGA AGGCACCAGGGGTGCC

TGCCTTTCCCCAGGGAATCCTCTCCAGATCTTAACCAAGAGCCCCTTGCAAAC

TCATTGGAAAAGTGCATGGTGTGTATTTTAGGGATTATGAGCTTCTTTCAAGG

ACCAAGAAATTTCCATTTGTGCTTCATGAAAAAAAACTTCTGGTTTTTTTCAT

BIOLOGICALLY ACTIVE BACTERICIDAL/PERMEABILITY-INCREASING PROTEIN FRAGMENTS

This is a Continuation of U.S. application Ser. No. 08/361,299, filed Jan. 23, 1995, now U.S. Pat. No. 5,748,408 which in turn is a continuation of U.S. application Ser. No. 08/007,837, filed Jan. 22, 1993 now U.S. Pat. No. 5,641,874 which in turn is a continuation of U.S. application Ser. No. 07/805,031, filed Dec. 11, 1991 (now issued Mar. 30, 1993 as U.S. Pat. No. 5,198,541), which in turn is a divisional of U.S. application Ser. No. 07/762,730, filed Sep. 17, 1991 now abandoned, which in turn is a file wrapper continuation of U.S. application Ser. No. 07/228,035, filed Aug. 5, 1988 (now abandoned), which in turn is a continuation-in-part of U.S. application Ser. No. 07/084,335, filed Aug. 11, 1987 (now abandoned).

The United States government has rights to this invention by virtue of research grant Nos. DK-05472 and AI-18571 from the National Institute of Health.

BACKGROUND OF THE INVENTION

The present invention pertains to biologically active, polypeptide fragments of mammalian bactericidal/permeability-increasing proteins and methods for making and using said fragments.

Bactericidal/permeability-increasing protein (BPI) is a 50 to 60 Kd protein, isolated from the granules of mammalian polymorphonuclear leukocytes (PMN) which are blood cells that are essential in the defense against invading microorganisms in mammals. BPI occurs only in cells of the myeloid series of blood cells, is produced at the promyelocytic/myelocytic stage of differentiation and is located in the primary granules in these cells.

BPI is a potent bactericidal agent active against a broad range of gram-negative bacterial species. It exhibits a high degree of specificity in its cytotoxic effect, i.e. 10–40 nM (0.5–2.0 micrograms), producing greater than 90% killing of $10^7$ sensitive bacteria whereas 100-fold higher concentrations of BPI are non-toxic for other microorganisms and eukaryotic cells. All available evidence suggests that in the intact PMN and in crude leukocyte fractions, BPI is the principal oxygen-independent agent present which is active against BPI-sensitive bacteria.

BPI isolated from both human and rabbit PMN has been purified to homogeneity. The molecular weight of human BPI is approximately 58,000 Daltons (58 kDa) and that of rabbit BPI is approximately 50 kDa. The amino acid composition of these two proteins is closely similar as is the amino acid sequence of their first 15 $NH_2$-terminal amino acid residues. Both proteins are highly basic, having an isoelectric point greater than 9.6.

The biological effects of BPI require attachment of the protein to the surface of the susceptible gram-negative bacteria. Initial binding of BPI to target cells involves electrostatic interactions between the basic protein and the negatively charged sites on the lipopolysaccharides (LPS) on the bacterial outer membrane and leads to an activation of bacterial enzymes that degrade phospholipids and peptidoglycans. The final stage of action is the actual killing of the bacteria by an as yet unknown mechanism. The closely similar amino acid composition and nearly identical bactericidal and membrane-perturbing properties of BPI purified from human and rabbit PMN suggest that this protein has been highly conserved during evolution and is an important member of the anti-bacterial arsenal of the mammalian PMN.

Due to its potent bactericidal action against gram-negative bacteria and lack of cytotoxicity towards other microorganisms and eukaryotic cells, it is envisioned that BPI may be employed as a chemotherapeutic agent and/or as a model for the design of new antibiotic agents. However, due to its large molecular weight (58 kDa for the human holoprotein), both sequencing and determination of the structural organization of BPI have been hampered (hereinafter the entire BPI molecule is referred to as the holoprotein). The possibility has been raised that, as in the case with other cytotoxic proteins, BPI has a structural organization where the different functions, namely binding, envelope-altering and killing reside in different domains within the BPI molecule. Although BPI fragments, obtained by digestion of the holoproteins with the proteolytic enzyme elastase, has been disclosed (Weiss, J. et al., *Clin. Res* 34: 537A, 1986), the fragments tested remained associated under the non-denaturing conditions employed. No biological activity was ascribed to any isolated fragments. Moreover, antibodies directed against the holoprotein did not recognize these fragments under denaturing conditions when analyzed using the well-known Western blotting procedure.

Therefore, in light of the above, there is a need in the art for biologically active peptide fragments of BPI for use as bactericidal/permeability increasing agents as well as therapeutic agents. Such fragments are also needed to provide sequence information on BPI to direct the design of future generations of antimicrobial agents specific for gram-negative bacteria and to be used as probes into the molecular organization of the holoproteins.

OBJECTS OF THE INVENTION

It is an object of the present invention to provide biologically active peptide fragments of mammalian BPI.

Another object of the present invention is to provide biologically active peptide fragments of mammalian BPI with improved antimicrobial effectiveness.

Yet another object of the present invention is to provide a process for the production of biologically active peptide fragments of mammalian BPI.

Yet another object of the present invention is to provide methods for treating mammals suffering from infections caused by gram-negative bacteria.

A further object of the present invention is to provide a method for increasing the permeability of gram-negative bacteria.

A still further object of the present invention is to increase the effectiveness of gram-negative bactericidal agents.

These and other objects of the present invention will be apparent to those of ordinary skill in the art in light of the present description, accompanying claims and appended drawings.

SUMMARY OF THE INVENTION

The present inventors have unexpectedly discovered biologically active fragments of mammalian BPI substantially shorter in length than the native BPI protein. Although these fragments are substantially smaller than the native molecule, they retain at least substantially all of the bactericidal and permeability-increasing properties of the intact protein.

The biologically active BPI fragments of the present invention can be produced by incubating a sample comprising the BPI holoprotein under BPI cleaving conditions and recovering biologically active fragments of the BPI holoprotein. The preferred BPI cleaving conditions include heating of the BPI holoprotein in an acceptable buffer for a time ranging between about 16 and 24 hours at a temperature between about 20° C. and about 37° C.

In another aspect, the present invention provides a method for treating mammals suffering from infections caused by gram-negative bacteria comprising administering to mammals in need of such treatment a gram-negative bactericidal-effective amount of at least one of the above-mentioned biologically active BPI fragments.

In another aspect, the present invention provides pharmaceutical formulations for treating infections in mammals caused by gram negative bacteria comprising a gram-negative bactericidal-effective amount of at least one of the biologically active BPI fragments or pharmaceutically-acceptable salts thereof.

In yet another aspect, the present invention provides a method for increasing the permeability of gram-negative bacteria comprising incubating the bacteria with a gram-negative-bacterial-permeability-increasing-effective amount of a biologically active fragment of BPI.

In still another aspect, the present invention provides a method for increasing the effectiveness of gram-negative bactericidal agents in mammals in need of such treatments, comprising co-administration of such agents with the biologically active fragments of BPI.

A still further aspect of the present invention is directed to a purified, isolated DNA sequence having the sequence set out in FIG. 5 or its complementary strand and DNA sequences hybridizing under stringent hybridization conditions with said DNA sequences. The DNA sequence encodes the human bactericidal/permeability-increasing protein.

BRIEF DESCRIPTION OF THE DRAWINGS

FIG. 5 (A–D), bottom line, shows the sequence of the cDNA encoding human BPI whereas printed above is the corresponding amino acid sequence. The two potential glycosylation sites are overlined.

DETAILED DESCRIPTION OF THE INVENTION

Figure 1:
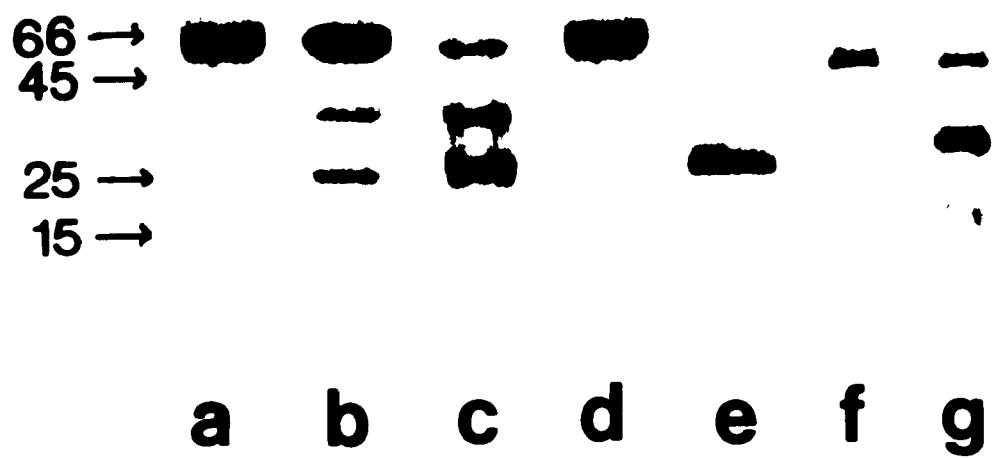
FIG. 1 is a photograph of a stained SDS-PAGE gel showing the production and purification of the human BPI fragment of a preferred embodiment of the present invention.

The present inventors have unexpectedly discovered biologically active fragments of BPI isolated from mammalian PMN. $NH_2$-terminal amino acid sequence analysis demonstrated that, in the case of human BPI, the fragment represents a portion of the BPI molecule proximal to the $NH_2$-terminus, as shown in Example 3 below. The fragment possesses all of the antibacterial and membrane permeability-increasing functions contained in the complete molecule but is substantially smaller (i.e. has a lower molecular weight) than the holoprotein. "Substantially smaller" is defined herein as being up to about half the size of the holoprotein. This is a most surprising finding because, in the case of other cellular toxins and proteins, the entire molecule is necessary for the full manifestation of their biological effects. For example, studies on a wide variety of bacterial and plant cytotoxins, such as diphtheria toxin, cholera toxin and ricin (toxins which do not demonstrate the unique specificity of the BPI holoprotein) have revealed that individual functions, such as binding or catalytic activity, can be expressed by isolated fragments, but that cytotoxicity (comprising both binding to a cell membrane and intracellular toxic activity) requires essentially the entire molecule.

The BPI fragments of the present invention are as potent as the holoprotein against rough E.coli, more potent than the holoprotein against the generally more resistant, smooth E.coli (on a molar basis), and retain the specificity of the holoprotein towards gram-negative bacteria. This is a particularly important finding because smooth gram-negative bacteria (smoothness being due to the presence of longer LPS chains in the bacterial cell membrane) generally are more pathogenic than their corresponding rough counterparts.

The distinctive size, chromatographic behavior (FIGS. 1 and 2 below) amino acid content (Table 1 below) and potency (see Example 4 below) firmly establish that the BPI fragment of the present invention is a molecular entity distinct from the holoprotein.

Non-limiting examples of the BPI fragments of the present invention are approximately 25 kDa for human and rabbit BPI. The human 25 kDa fragment of the preferred embodiment of the present invention was initially isolated after long-term storage (e.g. two months) of the purified holoprotein in a weakly acidic buffer (10mM ammonium acetate, pH4.6) and can be thus generated. However, it is preferable to produce the BPI fragments of the present invention by incubating the holoproteins in an acceptable buffer i.e., a buffer having sufficient buffering capacity at concentrations between about 10 and about 150 mM at a pH ranging between about 6.0 and about 8.0, such as Tris/HCl, phosphate, and preferably HEPES/NaOH (Sigma Chemicals, St. Louis, Mo.), or mixtures thereof. The preferred pH is 7.4. The incubations may be performed for a period of time broadly ranging between about 16 and 24 hours and preferably 18 hours, at a temperature ranging between about 20° C. and about 37° C. and preferably 37° C.. A particularly preferred condition comprises incubation in 0.1M HEPES/NaOH buffer, pH 7.4 for 18 hours at 37° C. This has led to the conversion of about 50% of the holoprotein into the biologically active fragments of the present invention. Reincubation of the recovered holoprotein, under these conditions again result in formation of the 25 kDa fragment.

The BPI holoproteins, used as starting materials for the production of the biologically active fragments of the present invention, can be obtained from mammalian cells of the myeloid series of blood cells, such as PMN. Although the fragments of the present invention are not limited to a particular mammalian species, it is preferable to employ such fragments isolated from a homologous mammalian species when treating bacterial infections caused by gram-negative bacteria.

In addition, the BPI holoprotein and/or the biologically active fragments of the present invention may be obtained using recombinant DNA techniques employing the sequence information presented below in Example 3 to synthesize DNA probes for the detection of DNA sequences coding for BPI in complementary DNA or genomic libraries using methods well-known in the art. The gene coding for the BPI holoprotein, or a portion of the gene coding for the 25 kDa fragment of the present invention (and possibly smaller biologically active fragments thereof) may be inserted into a suitable expression vector for the production of biologically active polypeptides.

In one embodiment, human BPI holoprotein can be obtained from PMN isolated from normal blood or from blood from patients with chronic myelocytic leukemia, as detailed in Example 1 below. Alternatively, human BPI can be extracted from the human leukemic cell line HL-60 (available as ATCC CCL 240, American Type Culture Collection, Rockville, Md.). The latter have been found to contain approximately 10 micrograms of BPI holoprotein per $10^8$ cells. Mature PMN of either normal or leukemic origin contain approximately 60 micrograms per $10^8$ cells of the BPI holoprotein and are therefore the preferred starting material.

Once obtained, the mammalian PMN can be fractionated using, for example, the procedures detailed below in Example 1 in order to obtain primary granules (or alternatively by extraction of whole cells with 0.16N sulfuric acid, as described in Elsbach. P. et al., *J. Biol. Chem.* 254:11000, 1979, incorporated by reference). Such primary granules isolated from PMN or leukemic cell lines contain the bulk of BPI holoprotein activity. The BPI holoprotein can then be extracted and purified using any technique known in the art which yields a biologically active BPI holoprotein. Although crude extracts obtained from such primary granules can be employed as starting materials for the production of the BPI fragments of the present invention, it is preferable to purify the holoprotein before generating the fragments. Preferred extraction and purification techniques for human and rabbit BPI holoprortein are described in Example 1 below.

The amounts of starting, purified, BPI holoprotein to be employed in practicing the present invention preferably should be at least 200 micrograms of purified holoprotein. Although it is possible to use smaller amounts of material, this may hamper the recovery of the biologically active fragments due to non-specific losses, as is true with many other biologically-active proteins, such as interferons..

Although not wishing to be bound by any theory of operation of the present invention, it is believed that the cleavage of the holoprotein to generate the biologically active fragments of the present invention is due to the presence of serine proteases.

The protein cleaving conditions necessary for the production of the biologically active BPI fragments of the present invention are broadly within the pH, temperature and time optima of such serine proteases, i.e. pH6.0–pH 8.0, 20° C.–37° C., 16–24 hours. Such incubation of the BPI holoprotein will produce cleavage at about 25 kDa from the $NH_2$-terminus of the holoproteins.

The biologically active BPI fragments of the present invention can be utilized for the treatment of mammals suffering from diseases caused by gram-negative bacteria such as, bacteremia or sepsis. Due to its exquisite selectivity and lack of cytotoxicity toward cells other than gram-negative bacteria, the BPI fragments of the present invention would be particularly useful as specific therapeutic agents. Currently gram-negative bacterial infections, such as those caused by *Escherichia coli,* various species of Salmonella, Klebsiella or Pseudomonas are treated with antibiotics, such as penicillin derivatives, aminoglycosides and chloramphenicol. The effectiveness of antibiotics is limited due to the fact that gram-negative bacilli tend to display significant intrinsic resistance to many currently available antibiotics and to readily develop further resistance due to the acquisition of resistance factor plasmids. Under appropriate selective conditions, rapid dissemination of multiple antibiotic resistance among a wide variety of gram-negative pathogens is known to occur.

When employed to treat bacteremia (i.e. the presence of bacteria in the blood stream) or sepsis (bacterial contamination of bodily fluids) caused by gram-negative bacteria, the BPI fragments of the present invention are preferably administered parenterally, and most preferably intravenously in amounts broadly ranging between about 1 microgram and 1000 micrograms and preferably between 10 and about 250 micrograms per treatment. The duration and number of treatments may vary from individual to individual, depending upon the severity of the illness. A typical treatment regime may comprise intravenous administration of about 100 micrograms of the BPI fragments three times a day. To help avoid rapid inactivation of the BPI fragments of the present invention (and indeed the holoproteins) which has been observed in vitro after incubation with serum, the BPI fragments may be coupled with physiologically-acceptable carriers, such as normally occurring serum proteins (e.g. albumin or lysozyme). The BPI fragments of the present invention could also be employed topically to treat mammals suffering from skin Affections caused by susceptible gram-negative bacteria which occur in bedridden patients suffering from decubitus ulcers (bed sores) or in burn patients. When employed as a topical antibacterial agent, the BPI fragments may be administered in the same dosages and frequency as described for parenteral administration above.

The BPI fragments of the present invention can be incorporated in pharmaceutical formulations to be used to treat mammals suffering from gram-negative bacterial infections. Pharmaceutical formulations comprising the BPI fragments of the present invention (or physiologically-acoeptable salts thereof) as at least one of the active ingredients, would in addition comprise pharmaceutically-acceptable carriers, diluents, fillers, salts and other materials well-known in the art depending upon the dosage form utilized. For example, preferred parenteral dosage forms would comprise a sterile isotonic saline solution, and many comprise between about 1 microgram and 1000 micrograms of the BPI fragments of the present invention covalently coupled to suitable physiologically-acceptable carriers, such as normally occurring serum proteins, for example lysozyme or albumin, to prevent their inactivation. For use in treating mammals with gram-negative bacterial infections in body fluids largely devoid of (lipo) proteins, such as urine, pharmaceutical formulations may comprise the above amounts of BPI fragments of the present invention and sterile, isotonic saline solutions for irrigation of the urinary tract.

In another preferred embodiment, the BPI fragments of the present invention in amounts ranging between 1 microgram and 1000 micrograms per dose, may be mixed with antibiotics and may be formulated in the same type of preparations used in antibiotic creams (such as Silvadene, Marion Laboratories, Kansas City, Mo., Terramycin, Pfipharmecs, New York, N.Y. or Achromycin, Lederle Laboratories, Pearle River, N.Y.) well-known in the art for topical administration.

In another preferred embodiment of the present invention pharmaceutical formulations for treating mammals suffering from gram-negative bacterial infections may contain the BPI fragments of the present invention in addition to standard amounts (well-known in the art) of antibiotics such as Penicillin-G (available from E. R. Squibb and Sons, Inc., Princeton, N.J.) or cephalosporins (available from Eli Lily & Co., Indianapolis, Ind.). In a particularly preferred embodiment, the BPI fragments of the present invention may be mixed with hydrophobic antibiotics, such as rifampicin (available as RIFAMPIN, CIBA Pharmaceutical CO., Summit, N.J.), and hydrophobic penicillins such as Penicillin-V Benzathine (Lederle Labs, Pearl River, N.Y.). The increased permeability of gram-negative bacteria after BPI treatment is expected to enhance the effectiveness of such antibiotics which cannot easily enter non-permeabilized bacteria.

The BPI fragments of the present invention are expected to be ideally-suited for co-treatment using any antibiotic, immune system cells or factors such as T-cells or interleukin-2, cytotoxic agents or the like, effective against gram-nagative bacteria. Because of the increased sensitivity to the fragments of the present invention of the more pathogenic, smooth, gram-negative bacteria, the BPI fragments of the present invention are expected to decrease resistance of such bacteria to such factors. Substantially simultaneous admistration of the fragments of the present invention and the antibiotic of choice is preferred.

An example of the above-mentioned embodiment is demonstrated in Example 4 below, wherein actinomycin D (which normally cannot enter and affect gram-negative bacteria due to its hydrophobic properties) significantly inhibited RNA and protein synthesis only in BPI-treated *E. coli*.

In addition, the present inventors have isolated the gene encoding the human BPI holoprotein and have identified and sequenced BPI cDNA isolated from human promyelocytic leukemia cells (HL-60). The nucleotide sequence of the cDNA and the corresponding amino acid sequence of the holoprotein are set out in FIG. 5.

Figure 5:
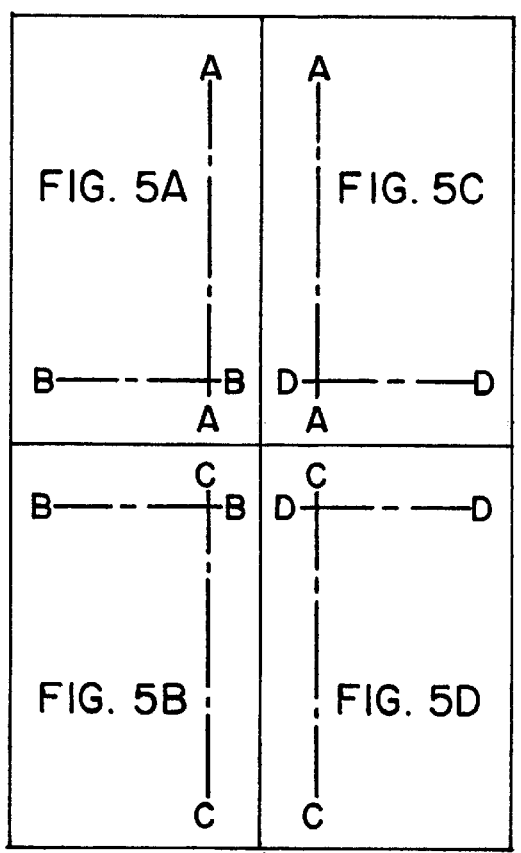
FIG. 5 is an index FIG. which shows the interrelationship of the sequence shown in FIG. 5 (A–D).

The sequence information contained in FIG. 5 can be employed to synthesize the 25 kDa, biologically active fragment of BPI. In this case, a vector can be generated comprising DNA residues 123 to about 759–780 (or amino acid residues 1 to about 210–220) of FIG. 5 using techniques well-known in the art. In addition, smaller sub-fragments of the cDNA of FIG. 5 can be generated using, for example, limited Ba131 nuclease digestion of the entire cDNA, to probe for the minimum sequences necessary for BPI biological activities mentioned above.

Alternatively, the BPI holoprotein can be obtained after synthesis by suitably transfected or transformed eukaryotic (mammalian or yeast) or prokaryotic cells and the biologically-active 25 kDa fragments mentioned above can be obtained using the techniques described in Example 2 below.

The present invention is described further below in specific examples which are intended to illustrate it without limiting its scope.

EXAMPLE 1

Isolation and Purification of Human BPI

Human leukocytes were obtained from heparin-treated (100–200 U.S.P. units/10 ml) peripheral blood collected by venipuncture from healthy donors and patients with chronic myelocytic leukemia.

Populations of human PMN were obtained in two ways. (1) PMN's were isolated by the dextran-sedimentation procedure, followed by centrifugation in an Isopaque-Ficoll gradient (Pharmacia Fine Chemicals, Piscataway, N.J.) as described (Boyum, A. J., *J. Clin. Lab. Invest.* Suppl. 97: 77–89, 1968, incorporated by reference). The leukocyte-rich plasma from healthy donors was first diluted with isotonic Krebs-ringer phosphate buffer (pH7.4) to a concentration of 10,000 to 20,000 cells/microliter before layering on the Isopaque-Ficoll mixture. The cells were washed twice in Krebs-ringer phosphate before use.

(2) Alternatively, leukocyte-rich plasma obtained by leukopheresis (using procedures well-known in the art) of 400 ml of venous blood, from a patient with chronic myelocytic leukemia, was sedimented directly at 1000×g for five minutes yielding $3.5 \times 10^{10}$ leukocytes, essentially all of which were PMN. These cells were washed twice with Krebs-ringer phosphate before homogenization.

For extraction of the human BPI holoprotein, the PMN were first disrupted in one of two ways: 1) Granule-rich fractions containing the bulk of the BPI activity, were obtained by homogenization at 0° C. of PMN suspended in 0.34 M sucrose ($2 \times 10^8$ cells/ml), as described in Weiss, J. et al., *J. Biol. Chem.* 253: 2664–2672, 1978, incorporated by reference, followed by centrifugation at 400×g for 10 and 20,000×g for 30 minutes at 4° C. The granule-rich pellet was extracted with approximately 10 volumes of 0.2 M sodium acetate (pH 4.0), overnight at 4° C. with continuous stirring. The extract was collected as a supernatant by centrifugation of the extract at 20,000×g for 30 minutes.

2) Alternatively, PMN (2–3×10$^8$ cells/ml) were disrupted in distilled water at 0° C. with a Potter-Elvejhem glass homogenizer and a motor-driven teflon pestle (Kontes; subsidiary of Kimble Div. of Owens, Ill.) and extracted at 0° C. for 30 minutes with 0.16N sulfuric acid to solubilize the BPI holoprotein. After centrifugation at 23,000×g for 20 minutes at 4° C. to sediment insoluble material, the extract was dialyzed against 200 mM sodium acetate/acetic acid buffer (pH 4.0). The BPI in these extracts was purified by gel filtration chromatography on a molecular sieving column (SEPHADEX G-75, superfine, Pharmacia Fine Chemicals, Piscataway, N.J.) at 4° C. The beads were prepared according to the manufacturer's instructions and equilibrated in the 0.2M sodium acetate (pH 4.0). Using this technique, substantially all of the BPI holoprotein activity was eluted as a single peak (fractions 35–39) corresponding to a discrete protein peak (5–6% of the total protein applied) just after the void volume.

The chromatographic fraction containing the human BPI holoprotein was subjected to further chromatography on an ion exchange resin (SP-SEPHADEX, Pharmacia Fine Chemicals, Piscataway, N.J.). Protein was applied to the column, equilibrated in 0.1N NaCl-0.2M sodium acetate/acetic acid buffer (pH4.6) and eluted with a stepwise gradient of buffered NaCl (0.3, 0.5 and 0.75M). Human BPI holoprotein eluted in the last step.

Purified human BPI holoprotein was then isolated by high performance liquid chromatography (HPLC) on a reverse phase C-4 (Vydac) column (Sota Chromatography, Crompand, N.Y.) using an HPLC system (Model 332, Beckman Instruments, Fullerton Calif.). The column used a linear gradient of acetonitrile (0–95% volume/volume, J. T. Baker Chemical Co., Philipsburg, N.J.) in 0.1% trifluoroacetic acid (TFA, Pierce Chemical Co., Rockford, Ill.). Human BPI eluted at about 70% acetonitrile and was dialyzed against approximately 50 volumes of 10 mM ammonium acetate/acetic acid buffer (pH4.6). Purified BPI was stored either in 0.2M sodium acetate/acetic acid buffer (pH 4.0) or in 10 mM ammonium acetate/acetic acid buffer (pH4.0) at 4° C.

EXAMPLE 2
Production of Human BPI Fragments

Purified human BPI holoprotein was incubate. in 0.1M HEPES-NaOH buffer, pH7.4 for 18 hours, and then analyzed by sodium dodecylsulfate polyacrylamide gel electrophoresis (SDS-PAGE) in 12% polyacrylamide gels using the buffer system containing 0.375M Tris/HCl and 0.1% SDS of Laemmli, U.K., *Nature* 227: 680–685 1970 incorporated by reference. The results are shown in FIG. 1. In FIG. 1, lanes A–E were stained using the well-known Coomassie blue technique and lanes F and G were silver stained using a commercial kit (Bio-Rad, Bio-Rad Labs, Richmond, Calif.).

Figure 2A:
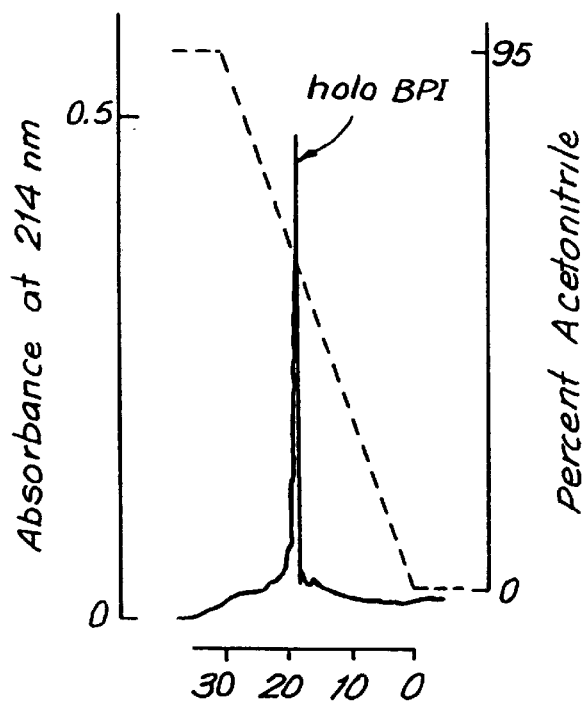
FIG. 2 is a graph showing the chromatographic behavior of the human BPI holoprotein (a) and human 25 kDa BPI fragment of the present invention (b) on reverse phase HPLC.
Figure 2B:
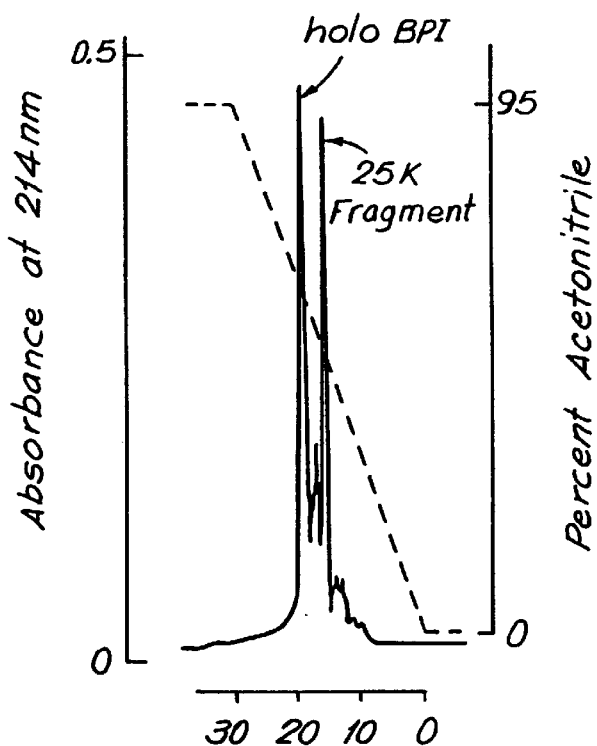

Upon incubation in 10 mM ammonium acetate buffer (pH 4.6) at 4° C. for two months, 10 micrograms of the purified human protein (FIG. 1, lane A) fragmented into two species of approximately 35 and 25 kDa (FIG. 1, lane B). Incubation of purified human BPI holoprotein (10 micrograms) for 24 hours at 37° C. in 0.1M HEPES/NaoH buffer, pH 7.4, enhanced the accumulation of the two species, particularly the 25 kDa species with the concomitant loss of the holoprotein (FIG. 1, lane C). Reverse phase HPLC of this incubated mixture, performed as described above for the holoprotein, yielded two major protein peaks, one co-eluting with native human BPI holoprotein and the other eluting slightly earlier (FIG. 2). Protein from the later peak migrated on SDS-PAGE as a single 60 kDa species and protein from the earlier peak migrated as a single 25 kDa species (FIG. 1, lanes D and E respectively). Fragmentation of the human BPI holoprotein and isolation of the 25 kDa fragment could be repeated with the recovered human holoprotein upon repetition of this procedure, confirming that the 25 kDa fragment was human BPI-derived.

In like manner, rabbit BPI holoprotein, purified as in Example 1 above (500 ng, FIG. 1, lane F) was fragmented after incubation for 18 hours at 37° C. in 0.1M HEPES-NaOH (pH7.4) into a 25 kDa species (FIG. 1, lane G).

EXAMPLE 3
NH$_2$-Terminal Amino Acid Composition and Sequence Analysis of BPI Fragments The human 25 kDa BPI fragment of the present invention was subjected to amino acid analysis, and the results were compared with the amino acid analysis of purified 60 kDa human holoprotein. Amino acid compositions were determined using a Waters Pico-Tag amino acid analyzer (Waters Associates, Milford, NA) as described (Bidlinamyer, B. A. et al., *J. Chrom.* 336: 93–104 1984 incorporated, by reference). Samples were pretreated in vacuo for 24 hours at 110° C. with 5.7N HCl containing 0.05% phenol. The results are shown in Table 1.

TABLE 1

Amino Acid Composition of the 25 kDa Fragment and of the Human BPI Holoprotein

| | 25 kDa Fragment | Human BPI Holoprotein |
|---|---|---|
| | (% of total) | |
| Asx | 8.7 | 9.1 |
| Glx | 8.8 | 8.9 |
| Ser | 15.2 | 8.8 |
| Gly | 7.1 | 6.4 |
| His | 2.9 | 2.8 |
| Arg | 3.6 | 3.7 |
| Thr | 3.5 | 4.6 |
| Ala | 4.1 | 6.0 |
| Pro | 5.0 | 8.1 |
| Tyr | 2.6 | 2.7 |
| Val | 5.8 | 7.3 |
| Met | 2.3 | 2.4 |
| Ile | 7.3 | 5.0 |
| Leu | 7.7 | 10.3 |
| Phe | 4.2 | 6.1 |
| Lys | 11.4 | 7.6 |

The values shown above represent the mole fraction (%) of each amino acid and are the mean of three independent determinations "Asx" stands for asparagine and/or aspartic acid and "Glx" stands for glutamine or glutamic acid.

Amino acid analysis showed that the human 25 kDa fragment was enriched in lysine and serine and contained less non-polar residues when compared with the holoprotein (Table 1).

NH$_2$-terminal sequence analysis of the human BPI fragment of the present invention and of the holoprotein were performed using the well-known sequential Edman degradation technique (Edman, P. *Eur. J. Biochem.* 1:80–91, 1967, incorporated by reference) using an amino acid sequencer (Beckman, Model 890C, Beckman Instruments Inc., Fullerton, Calif.) for the holoprotein or a gas phase sequencer (Applied Biosystems, Model 470A, Applied Biosystems, Inc., Foster City, Calif.) for the fragment. Phenylthiohydantoin derivatives of amino acids released sequentially by the Edman degradation process were analyzed by reverse-phase HPLC using an 150 mm C-18 column for human BPI (IBM Instruments Inc., Willingford, Conn.) or an ODS column for the fragment of the present invention (Dupont Zorbax ODS column, E.I. Dupont de Nemours, Wilmington, Del.). The results are shown in Table 2 below.

TABLE 2

| Holoprotein | V N P G V V V R I S Q K G L D Y A S Q Q |
|---|---|
| 25 Kd Fragment | V N P G V V V R I S Q K G L D Y A S Q Q |

V = Val, N = Asn, P = Pro, G = Gly, R = Arg, I = Ile,

Q = Gln, K = Lys, L = Leu, A = Ala, S = Ser

As can be seen from the data in Table 2, the NH$_2$-terminal amino acid sequence of the human 25 kDa fragment of the present invention and the holoprotein derived from human PMN were identical in the first 20 amino acid residues, indicating that the fragment was the NH$_2$-terminal portion of the human holoprotein.

EXAMPLE 4
Biological Properties of the BPI Fragment of the Present Invention

The antibacterial effects of the 25 kDa human BPI fragment of the present invention were compared with the known activities of the holoprotein. *E. coli* J5 (obtained from Dr. L. Leive, NIH Bethesda, Md.) which produces short-chain lipopolysaccharides (LPS) in galactose-free culture medium, were grown overnight and then subcultured at 37° C. in triethanolamine-buffered media as described in Simon. E. G. et al., (*Proc. Nat. Acad. Sci.* USA 51:877, 1964, incorporated by reference). 5×10$^6$ *E. coli* J5 were incubated in a volume of 250 microliters with increasing amounts of either the human holoprotein or the human 25 kDa fragment of the present invention. The effects on bacterial viability were determined either by (1) diluting an aliquot (5×10$^5$ bacteria) of the incubation mixture into 2 ml of nutrient broth (Difco Laboratories, Detroit, Mich.) and measuring bacterial growth (absorbance at 550 nM using a standard spectrophotometer after approximately 4 hours at 37° C.); or (2) plating diluted samples on nutrient agar and counting bacterial colonies after overnight incubation at 37° C. The results are presented in FIG. 3. In FIG. 3, open circles represent BPI holoprotein-treated bacteria and closed circles represent bacteria treated with the human 25 kDa fragment of the present invention.

Figure 3A:
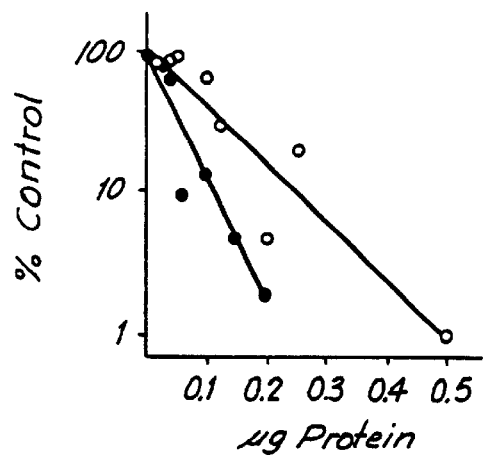
FIG. 3 is a series of graphs comparing the biological activities of the 25 kDa human BPI fragment of the present invention and the holoprotein toward E. coli J5. (A) bactericidal activity; (B) effect on bacterial protein synthesis; (C) permeability increasing activity; and (D) phospholipase activation.

FIG. 3A shows that the isolated 25 kDa fragment of the present invention killed *E. coli* J5, a strain of bacteria highly sensitive to the holoprotein, in a dose-dependent manner. A linear regression analysis of the data presented in FIG. 3A further showed that the fragment was about twice as potent as the holoprotein on a mass basis, meaning that it is about equally potent on a molar basis because the fragment is about half the size of the holoprotein (FIG. 3A).

Figure 3B:
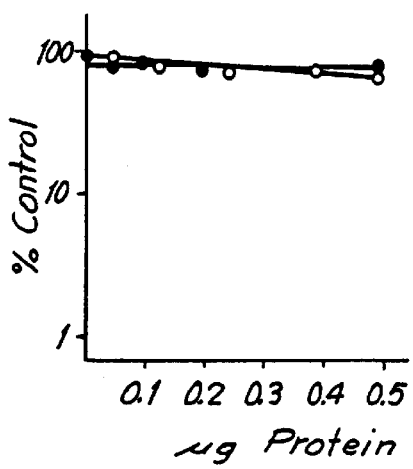
Figure 3C:
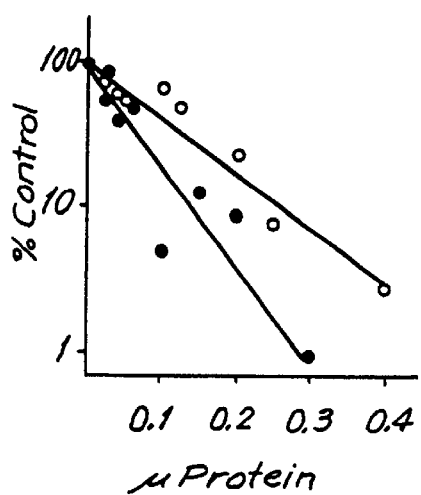

Killing of *E. coli* by mammalian BPI is initially accompanied by discrete alterations of the outer envelope without causing any apparent damage to the bacterial biosynthetic machinery. FIG. 3B shows that even at almost fully lethal doses, both the human holoprotein and the human 25 kDa fragment of the present invention caused little inhibition of bacterial protein synthesis. In contrast, both the fragment and the holoprotein caused nearly a complete inhibition of *E. coli* J5 protein synthesis when administered in the presence of 50 micrograms/ml of the antibiotic actinomycin D (Merck, Sharp and Dohme, St. Louis, Mo., FIG. 3C). This effect of actinomycin D reflects increased permeability of the outer membrane of the bacteria, permitting the entry of the normally impermeant actinomycin D into the cell where it inhibited RNA and, consequently, protein synthesis. The dose-dependence of the permeability-increasing effect of the fragment of the present invention and the holoprotein was the same as that shown for the bactericidal activity above, and demonstrated that in this respect also the fragment was twice as active as the holoprotein, on a mass basis.

In order to compare the effects of the fragment of the present invention with the holoprotein on bacterial phospholipids, bacteria were prelabeled during growth with (1-$^{14}$C)-oleic acid (New England Nuclear, Boston, Mass.) as described in Elsbach. P. et al., *J. Biol Chem.* 254: 11000–11009, 1979 incorporated by reference. Incubation mixtures were supplemented with 0.4% bovine serum albumin (W/V) to capture phospholipid breakdown products ($^{14}$C-free fatty acids and $^{14}$C-lysocompounds) permitting their separation from unhydrolyzed bacterial $^{14}$C-phospholipids by filtration through a membrane filter (Millipore HAWP, Millipore Corp. Bedford, Mass.) to measure phospholipid degradation. The results are shown in FIG. 3D.

Figure 3D:
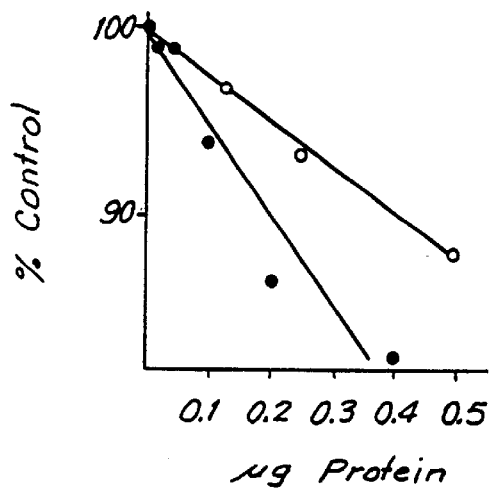

As shown in FIG. 3D, the dose-dependent activation of bacterial phospholipid degrading enzymes by the holoprotein was also produced by the 25 kDa fragment of the present invention, again requiring only half the mass of protein for a comparable effect.

The action of the BPI holoprotein on *E. coli* is hindered by the presence in the bacterial outer membrane of lipopolysaccharides with long polysaccharide chains ("smooth strains"). The effectiveness of the 25 kDa fragment of the present invention towards a smooth *E. coli* strain (0111:B4) was compared with that of the holoprotein. *E. coli*

0111:B4 is a smooth strain bearing longer polysaccharide chains than E. coli J5. Bacteria (1×10⁶) were incubated in 125 microliter mixtures with increasing amounts of the BPI holoprotein or the 25 kDa fragment of the present invention. Bacterial viability was measured as above and is expressed as percent of viability of bacteria incubated alone (without any additions). The results are shown in FIG. 4.

Figure 4:
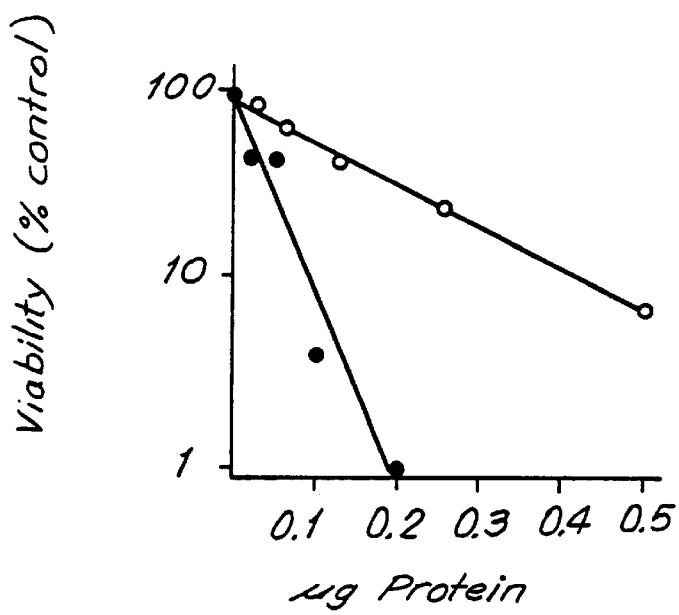
FIG. 4 is a graph comparing the bactericidal effect of the 25 kDa human BPI fragment of the present invention and the holoprotein on E.coli 0111:B4.

As can be seen in FIG. 4, the 25 kDa fragment of the present invention (closed circles) was about five times more potent than the holoprotein (open circles) towards E. coli 0111:B4. The five fold enhancement in activity of the 25 kDa fragment of the present invention with respect to the holoprotein, suggests that the smaller size of the fragment of the present invention is a factor in facilitating access of the fragment to binding sites at the base of the LPS polysaccharide chain.

In order to determine if the human 25 kDa fragment of the present invention retained the same cytotoxic specificity towards gram-negative bacteria as the holoprotein, the activities of the 25 kDa fragment and the holoprotein toward a gram-positive bacterium, *Micrococcus lysodeikticus* (obtained from Dr. M. Salton, New York University, New York, N.Y.) were compared. The bacteria were grown in brain heart infusion broth (Difco Laboratories, Detroit, Mich.) at 37° C. Bacterial viability was measured as above for E. coli.

Neither the human 25 kDa fragment of the present invention (5–10 micrograms) nor the holoprotein (10–20 micrograms) produced any effect on the viability of *Micrococcus lysodeikticus,* even at doses twenty times greater than those that are fully lethal towards gram-negative E. coli J5.

The data presented above demonstrate that the spectrum and potency of the antibacterial activities of the human 25 kDa BPI fragment of the present invention are at least equal to and sometimes substantially greater than those of the holoprotein. The data indicate that all of the molecular determinants required for BPI cytotoxicity reside within the portion of the BPI molecule included in the fragment of the present invention.

EXAMPLE 5

Cloning of the cDNA of Human BPI and Identification of the Amino Acid Sequence

Two synthetic oligonucleotides were designed to encode the 33 amino terminal residues of human BPI. The probes BPI-1 (GTCAATCCTGGTGTTGTGGTCAGGATCTCTCAGAAGGGC) and BPI-2 (GCAAGGCACAGCTGCCCTGCAGAAGGAGCTGAAGAGG) were each designed to encode half of the partially known human BPI sequence as previously disclosed in Ooi, C. E. et al., (*J. Biol. Chem.* 262: 14891–14894, 1987). The probes were kinase labeled with ³²P using standard techniques well-known in the art and used to independently screen a human genomic liver library as disclosed in Lawn, R. M. et al. (*Cell* 15: 1157–1174, 1978). Six clones were identified among 500,000 plaques which hybridized independently with each probe. The hybridizing region of one of these clones was sequenced and clearly encoded the amino terminal end of human BPI. This sequence was interrupted by an intron or intervening sequence but nevertheless predicted an additional 22 amino acid residues which preceded the next intron.

Based on the gene sequence, a new DNA probe was then synthesized which corresponded exactly to the encoded 55 amino terminal amino acid residues. This probe was used to screen a small cDNA library prepared from human HL-60 cells (available as ATCC CCL 240, American Type Culture Collection, Rockville, Md.) induced with dimethylsulfoxide, DMSO. In the library of the 300,000 plaques, 4 clones were isolated which hybridized with the exact probe. DNA from the clones was isolated and the hybridizing regions were sequenced by the dideoxy chain termination technique of Smith. A. J. H. (*Meth. Enzym.* 65: 560–580, 1980). The sequence of the longest clone is presented in FIG. 5.

As shown in FIG. 5, the sequence predicts a 31 amino acid signal peptide, followed by a 456 residue mature protein. The amino terminal sequence determined by protein sequencing of human BPI matches the encoded cDNA exactly. Furthermore, the deduced amino acid composition of the encoded protein corrsponds closely to the amino acid composition determined for purified human BPI as disclosed in Ooi. C. E. et al., supra. The encoded sequence predicts a protein of 50.6 kD; the estimated molecular size of purified human BPI is approximately 58 kD. This difference in the apparent size may reflect the presence of two potential N-linked glycosylation sites at positions 122 and 249 of the protein (indicated by overlines in FIG. 5).

To further demonstrate that this cDNA encoded human BPI, its expression was engineered in mammalian cells. The entire cDNA was subcloned in a mammalian cell expression vector (Wood, W. I. et al., *Nature* 312: 330–337, 1984), and then transfected into a human kidney cell line. Small amounts of recombinant BPI were transiently produced and characterized by Western Blotting techniques, showing an immunoreactive band with a mobility identical to that of native human BPI (results not shown).

The natural expression of BPI in various human tissues was then analyzed by Northern Blot hybridization. RNA was prepared from various tissues (Chirgwin, J. M. et al., *Biochem.* 24: 5294–5299, 1979), passed over oligo-dT-cellulose and electrophoresed through a formaldehyde agarose gel (Dobner. P. R. et al., *Proc. Nat. Acad. Sci. USA* 78: 2230–2234, 1981). The gel was transferred to nitrocellulose as described (Thomas, P. S., *Proc. Nat. Acad. Sci. USA* 77: 5201–5205, 1980) and hybridized under stringent conditions with BPI cDNA.

Figure 6:
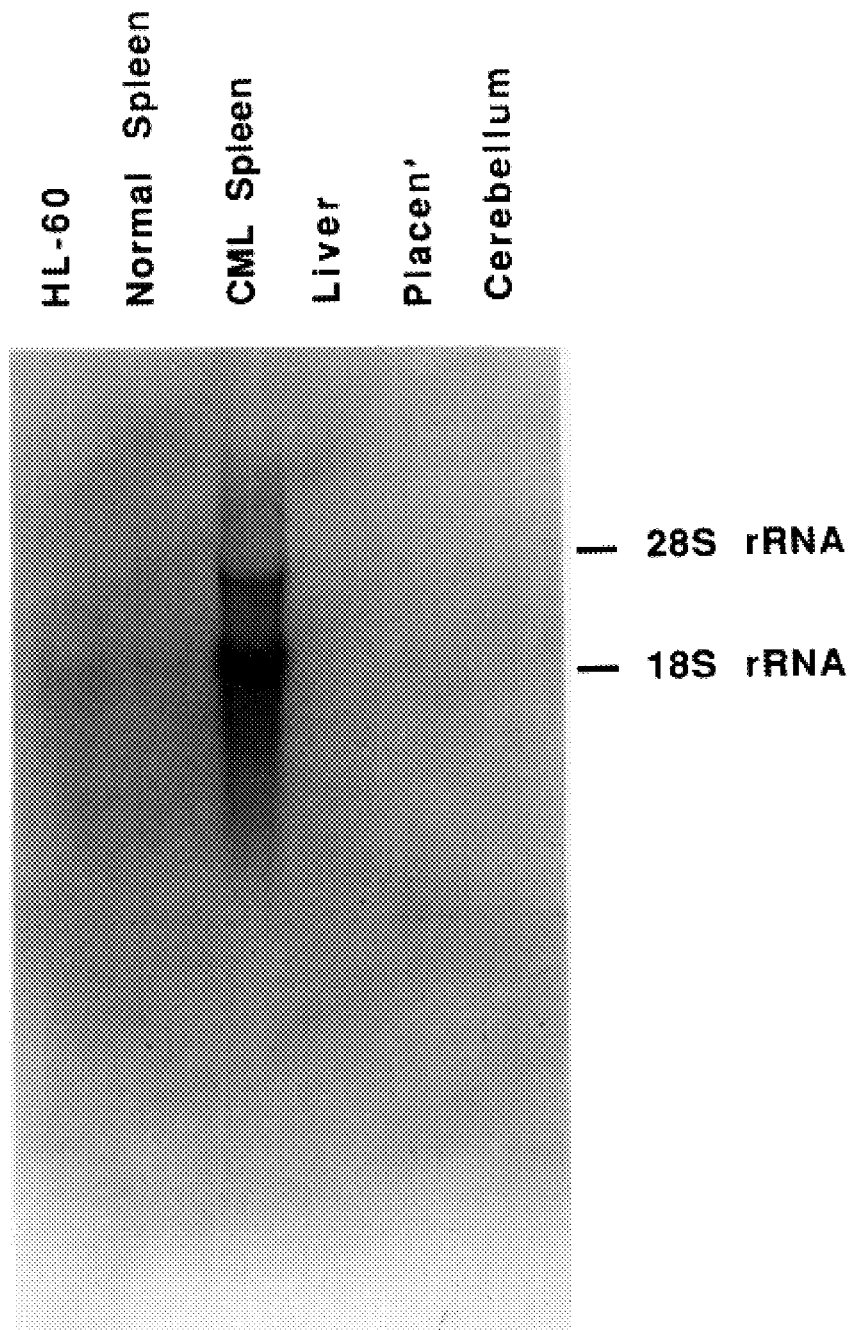
FIG. 6 is an autoradiogram of a Northern blot analysis of human BPI mRNA.

The BPI cDNA probe hybridized well with mRNA prepared from the spleen of a patient with chronic myelogenous leukemia. The spleen was heavily infiltrated with immature myeloid cells. The size of the hybridizing signal was approximately 2,000 bases in length, suggesting that the CDNA sequence presented in FIG. 5 was full length. The BPI probe did not hybridize with mRNA from normal spleen, mature peripheral blood leukocytes, liver, kidney, or brain (FIG. 6). This result is in agreement with previous observations on the location of BPI in various cell types and tissues; the presence of BPI has been previously shown to be restricted to cells of the myeloid series. The BPI cDNA was also used as a probe in Southern hybridizations of human genomic DNA. DNA was isolated from human peripheral blood leukocytes, as described in Blin, N. et al. (*Nuc. Acids Res.* 3: 2303–2308, 1976), digested with restriction endonucleases Eco RI, BamHI and HindIII, and fractionated on a 1% agarose gel. The DNA was transferred to nitrocellulose (as described in Southern, E. M., *J. Molec. Biol.* 98: 503–517, 1975) and hybridized with a 5' end fragment of the BPI cDNA probe under stringent conditions (as described in Maniatis et al., Molecular cloning, a laboratory Manual, pp. 387–389, C.old Spring Harbor Laboratories, N.Y., 1982, incorporated by reference).

Figure 7:
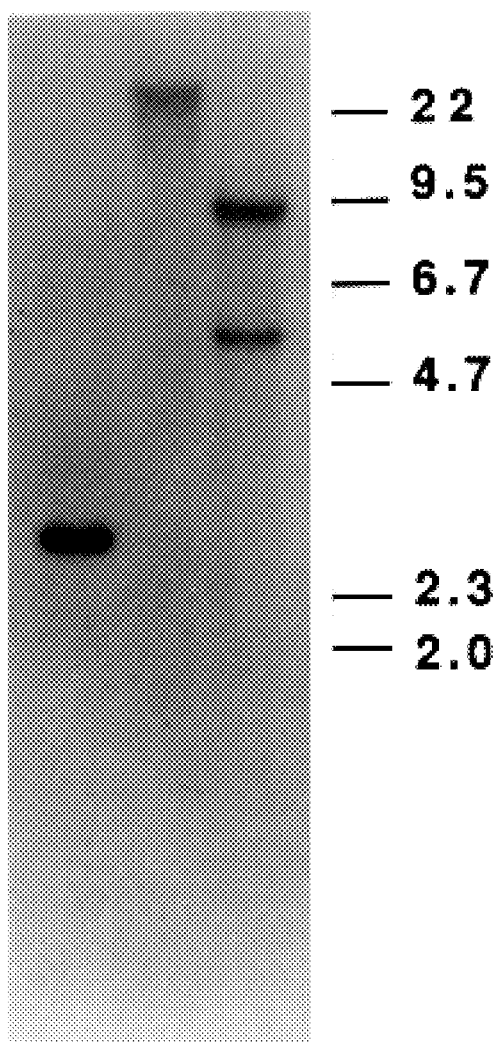
FIG. 7 is an autoradiogram of a Southern blot analysis of human genomic DNA using a BPI cDNA probe.

As shown in FIG. 7, a single hybridizing band was observed in restriction digests using Eco RI and BamHI when the 5' end of the BPI cDNA was utilized as a probe. This suggested that BPI was encoded by a single gene.

The primary structure of the human BPI protein sequence reveals several features which may be critical for its function As mentioned above, an amino terminal 25 kD fragment contains all of the bactericidal activity of the holoprotein. A clear charge asymmetry can be observed when the amino terminal 25 kD fragment is compared with the holoprotein. The amino terminal end contains 16 more basic than acidic residues (28 lysine/argine vs. 12 aspartate/glutamate), while the carboxy terminal end is slightly acidic (20 basic vs. 22 acidic residues). The very basic nature of the amino terminal domain may promote an electrostatic interaction of BPI with the negatively charged LPS on the bacterial envelope.

Paper Example I
Co-Treatment of Gram-Negative Bacteria with the Human BPI Fragment and Penicillins The human BPI fragment of the present invention will be used to test the effectiveness of compositions containing the fragments and Penicillin-G or a hydrophobic derivative, Penicillin-V. Both smooth (*E. coli* 0111:B4) and rough (*E. coli* J5) gram-negative bacteria will be seeded and incubated as in Example 3 above with serial two-fold dilutions containing: the human 25 kDa BPI fragment of the present invention (1microgram–1000 micrograms) alone, Penicillin-G (3000–300,000 units) alone, Penicillin-V Benzathine (3000–300,000 units) alone and compositions containing the same concentrations of the above as mixtures, e.g. the BPI fragment plus Penicillin-G and the BPI fragment plus Penicillin-V. Bacterial viability will be monitored as above in Example 3.

It is expected that lower amounts of both of the penicillins will be effective in killing both smooth and rough *E. coli* strains in the presence of the human 25 kDa BPI fragments showing the efficacy of this embodiment of the present invention.

What is claimed is:

1. A method for producing human bactericidal/permeability-increasing protein (BPI) comprising the steps of:
   (a) growing in a suitable culture medium host cells transformed or transfected to express BPI encoded by nucleotides 124 through 1491 of the DNA sequence set forth in FIG. 5 or its fully complementary strand, or a human BPI DNA sequence that hybridizes under stringent hybridization conditions with the DNA sequence set forth in FIG. 5 or its fully complementary strand; and
   (b) isolating BPI from said host cells or the culture medium.

2. The method of claim 1 wherein the cells are transfected or transformed with nucleotides 124 through 1491 of the DNA sequence set forth in FIG. 5.

3. Host cells transformed or transfected to express BPI encoded by nucleotides 124 through 1491 of the DNA sequence set forth in FIG. 5 or its fully complementary strand, or a human BPI DNA sequence that hybridizes under stringent hybridization conditions with the DNA sequence set forth in FIG. 5 or its fully complementary strand.

* * * * *